(12) United States Patent
Proppert et al.

(10) Patent No.: US 6,833,451 B2
(45) Date of Patent: Dec. 21, 2004

(54) **LIPOPOLYSACCHARIDES (LPS) EXTRACTED FROM *ESCHERICHIA COLI***

(75) Inventors: Hans Proppert, Hagen (DE); Jürgen Malinka, Selm (DE); Jürgen Schulze, Bergholz-Rehbrucke (DE); Ulrich Sonnenborn, Bochum (DE); Ulrich Zähringer, Garbsen (DE); Artur Ulmer, Nienwohld (DE); Ernst Theodor Rietschel, Hamburg (DE)

(73) Assignee: Pharma-Zentrale GmbH (DE)

( * ) Notice: Subject to any disclaimer, the term of this patent is extended or adjusted under 35 U.S.C. 154(b) by 257 days.

(21) Appl. No.: 10/239,254

(22) PCT Filed: Mar. 20, 2001

(86) PCT No.: PCT/EP01/03153

§ 371 (c)(1),
(2), (4) Date: Dec. 23, 2002

(87) PCT Pub. No.: WO01/70756

PCT Pub. Date: Sep. 27, 2001

(65) Prior Publication Data

US 2003/0108573 A1 Jun. 12, 2003

(30) Foreign Application Priority Data

Mar. 20, 2000 (DE) .......................................... 100 13 539

(51) Int. Cl.[7] .......................... C08B 37/00; C07H 5/06; A61K 31/739; C12P 19/26; G01N 33/554
(52) U.S. Cl. ........................ 536/55.1; 536/53; 536/117; 514/54; 424/241.1; 435/84
(58) Field of Search ............................ 514/54; 536/53, 536/55.1, 117, 18.7, 115; 424/241.1; 435/84

(56) References Cited

FOREIGN PATENT DOCUMENTS

DE          19844191          3/2000

OTHER PUBLICATIONS

Jansson et al., Carbohydrate Research, 131 (1984) 277–283.*

P.–E. Jansson et al., Structural Studies of the *Escherichia coli* O–Antigen 6, Carbohydrate Research, 1984, 277–283, Elsevier Science Publishers, The Netherlands.

J.A. Yethon et al., Involvement of waaY, waaQ, and waaP in the Modification of *Escherichia coli* Lipopolysaccharide and Their Role in the Formation of a Stable Outer Membrane, The Journal of Biological Chemistry, 1998, 26310–26316, The American Society for Biochemistry and Molecular Biology, Inc.

Structure and Conformation of the Lipid A Component of Lipopolysaccharides, Handbook of Endotoxin, 1984, 187–220, vol. 1, Elsevier, Amsterdam.

Chemical Structure of the Core Region of Lipopolysaccharides, Bacterial Endotoxic Lipopolysaccharides, 135–170, vol. I, CRC Press, Boca Raton.

* cited by examiner

*Primary Examiner*—Samuel Barts
*Assistant Examiner*—Michael C. Henry
(74) *Attorney, Agent, or Firm*—Lerner, David, Littenberg, Krumholz & Mentlik, LLP

(57) ABSTRACT

Lipopolysaccharides and processes for producting the lipopolysaccharides are provided. The lipopolysaccharide has a lipid A portion, a core oligosaccharide portion, and an O-specific chain having a single repeating unit 06. A lipopolysaccharide may be produced by washing and drying and *E. coli* bacterial mass, subjecting the washed and dried bacterial mass to a phenol/water extraction, and treating the extract with RNases, DNases, and proteinase K.

9 Claims, 7 Drawing Sheets

FIG. 1

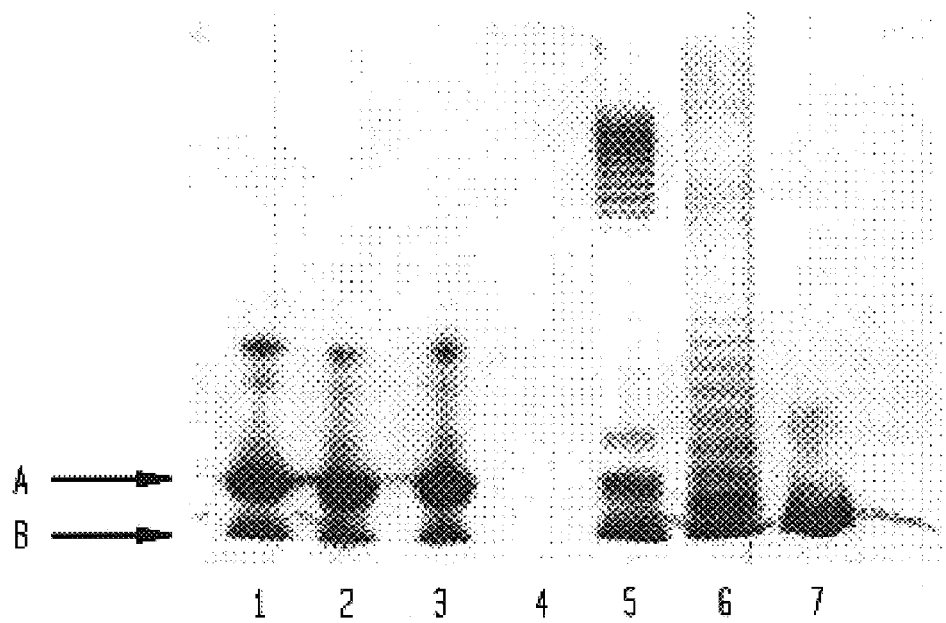

SDS-PAGE of Escherichia coli DSM 6601 (16% separating gel).

(1) LPS preparation 1 (phenol/water extract UM II.82); (2) LPS preparation 2; (3) LPS preparation 3; (4) free; (5) E. coli O111 LPS; (6) Pseudomonas aeruginosa Fischer type 2 LPS; (7) Salmonella minnesota R60 LPS. Arrows point to the LPS bands of core oligosaccharide and a repeating unit (R/S [sic] mutant, arrow A) and to an LPS with a complete core oligosaccharide (arrow B).

FIG. 2

Structure of the O antigen of E. coli O6. Cited from: Jansson, P. e., Lindberg, B., Lönngren, J., Ortega, C., Svenson, S.B. (1984) Carbohydr. Res., 131, 277-283.

$$-3)\text{-}\beta\text{-Man-}(1\rightarrow 4)\text{-}\beta\text{-Man-}(1\rightarrow 3)\text{-}\alpha\text{-GlcNAc-}(1\rightarrow 4)\text{-}\alpha\text{-GalNAc-}(1\rightarrow$$
$$2$$
$$\uparrow$$
$$1$$
$$\beta\text{-Glc}$$

All sugars are present in the D-pyranose form.
In contrast to the structure of the O-specific chain of E-coli O6 published by Jannson et al., the first repeating unit of the S/R mutants of E. coli DSM 6601 is linked by a $\beta$-glycosidic bond and was determined as such for the first time in the present patent, together with the site of substitution at the side-chain glucose ($\text{Glc}^{III}$) of the core oligosaccharide (see Figure 4).

FIG. 3

Structure of the hexaacyl lipid A of Escherichia coli.
(Zähringer, U., Lindner, B. and E. T. Rietschel, Molecular Structure of Lipid A, the Endotoxic Center of Bacterial Lipopolysaccharides, Adv. Carbohydr. Chem. Biochem., 50 (1994) 211-276)

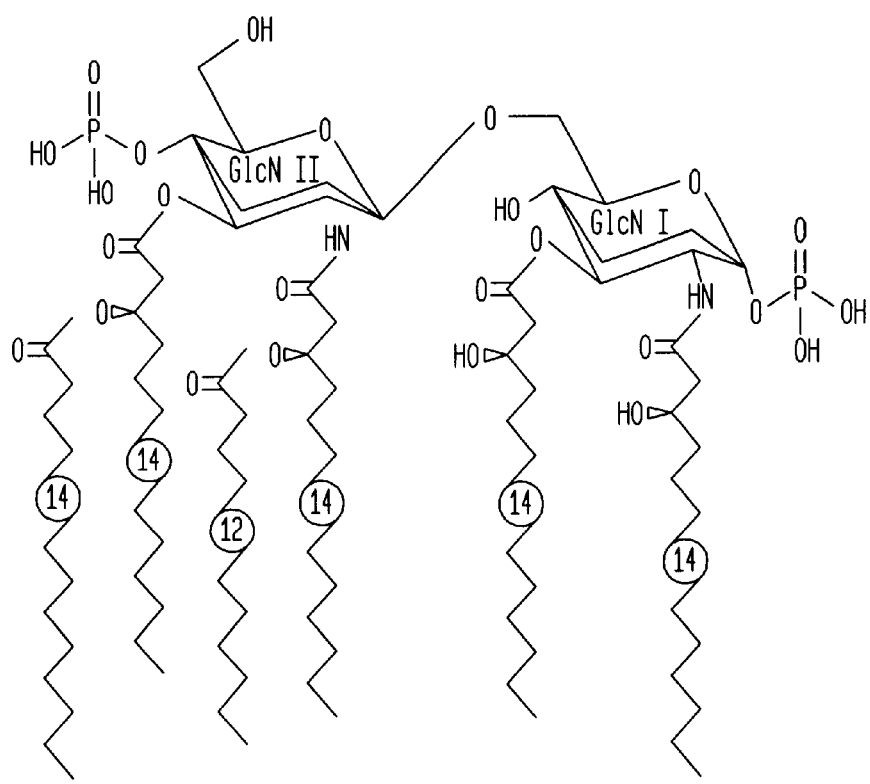

The numbers in the circles indicate the number of carbon atoms in the given fatty acid. The free hydroxyl group of the GlcN (II) represents the bonding site for the Kdo (I) of the core oligosaccharide.

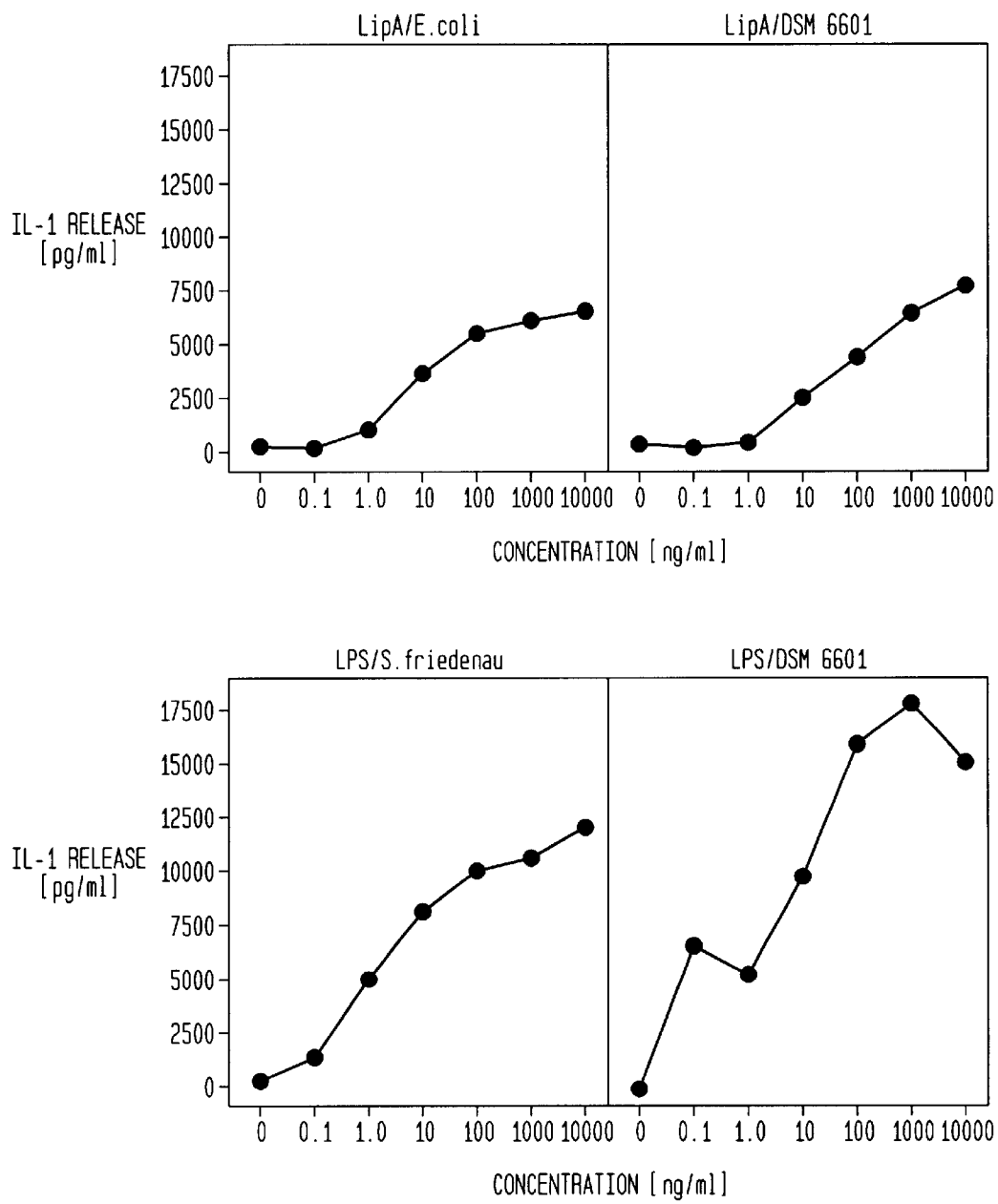

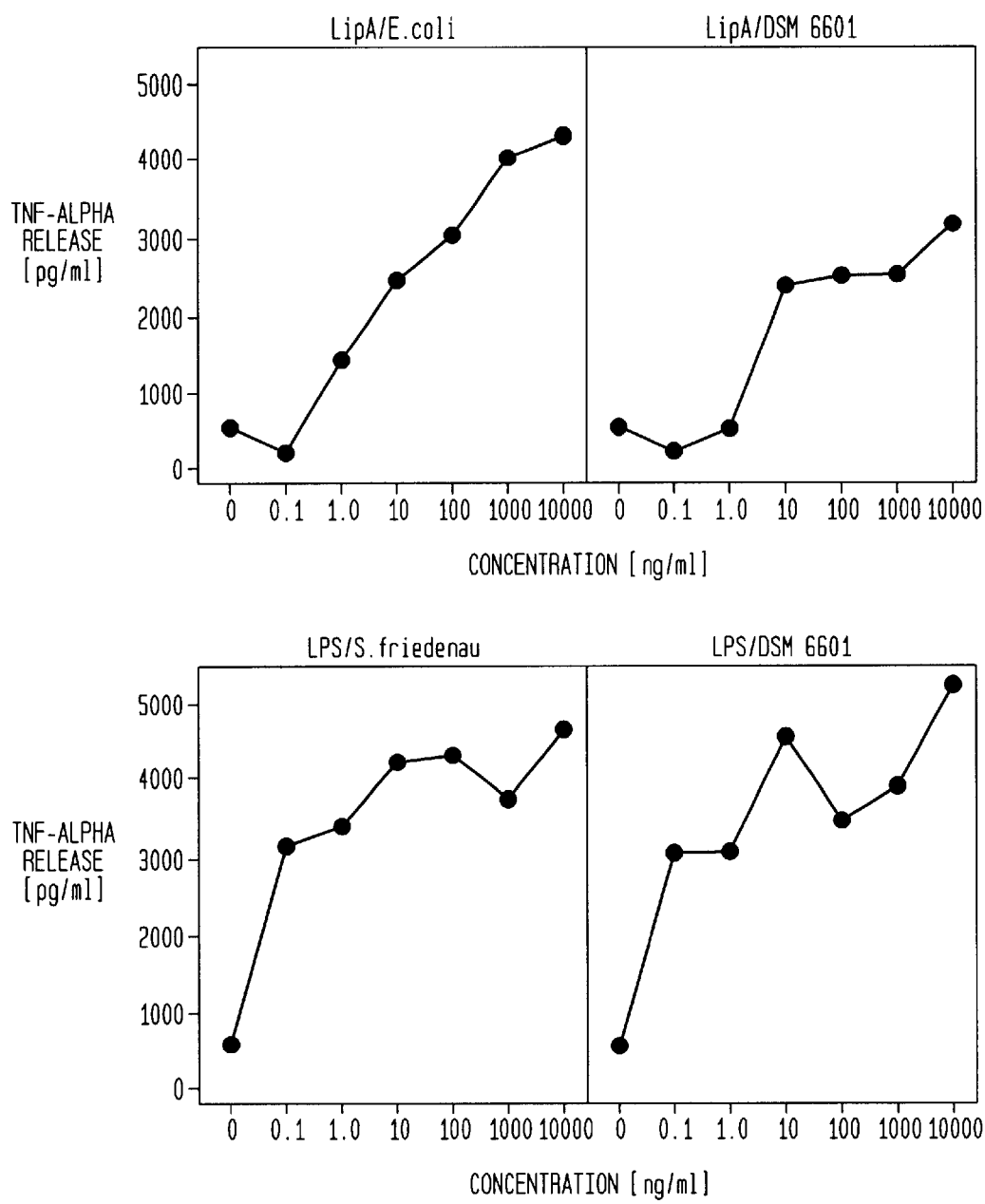

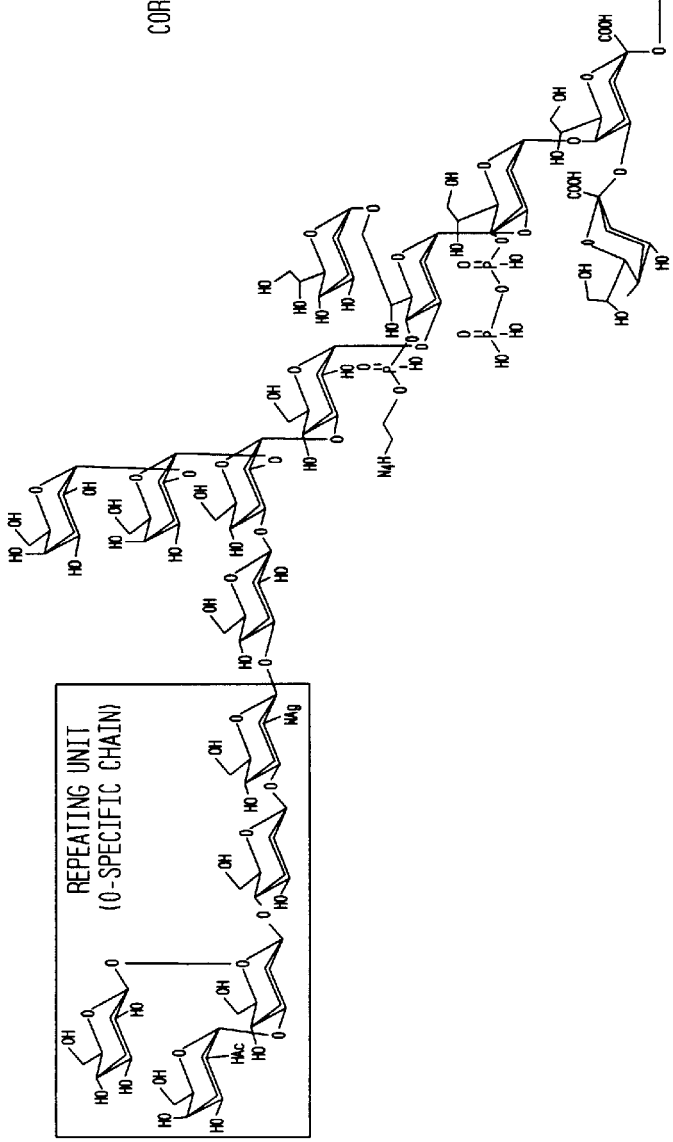
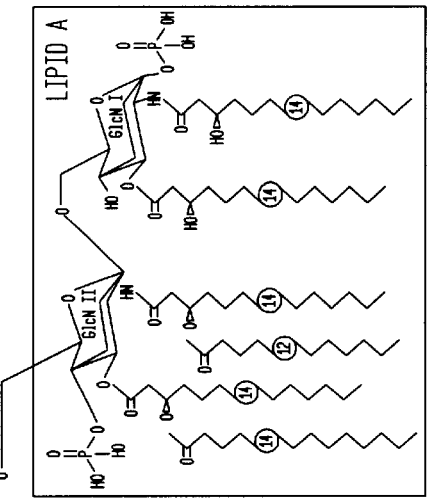

FIG. 7
CORE OLIGOSACCHARIDE

Structure of the complete lippopolysaccharide (LPS) of E. Coli DSM 6601.

The phosphate substituents P and Etn in the two heptoses $Hep^I$ and $Hep^{II}$ are not stoichiometric in the core oligosaccharide and are therefore indicated by a broken line.

The position and anomeric bond of the $Kdo^I$ to the lipid A are analogous to other E. coli LPS structures, likewise the position and anomeric bond of the $Kdo^{II}$.

LIPOPOLYSACCHARIDES (LPS) EXTRACTED FROM ESCHERICHIA COLI

This is the national phase Application of PCT EP01/03153 filed, Mar. 20, 2001.

BACKGROUND OF THE INVENTION

The invention concerns new lipopolysaccharides extracted from *E. coli*.

Endotoxins are bacterial structural components, which, unlike exotoxins, are not secreted, but rather are released, especially following autolysis. The classic endotoxins are heat-stable lipopolysaccharides (LPS) from the outer cell membrane of gram-negative bacteria. LPS consists of lipid A, which is responsible for the toxic effect of LPS, a core oligosaccharide and an O-specific chain.

In macroorganisms, endotoxins stimulate the production of immune system mediators, such as interleukin-1 (IL-1) and tumor necrosis factor (TNFα).

Many studies have already been conducted on the composition of the endotoxins of enterobacteria, especially *E. coli*, in which it was determined that S/R mutants generally contain only one repeating unit of their O specific chain (cf. FIG. 1). It is assumed that in these cases, the gene that codes for the polymerizing enzyme of the O-specific chain is defective, and therefore only one repeating unit it transferred to the core oligosaccharide. LPS structures of a similar type but different structure are also commonly found in bacteria that are pathogenic in man, such as Neisseria, Vibrio, Campylobacter, Helicobacter, etc. These bacteria have an LPS which allows them to evade the immune defense of the host by means of a special molecular mimicry, including the presence of sialic acid and oligosaccharides that contain sialic acid, which resemble glycoproteins and glycolipids in mammals. The 06 serotype was determined for *E. coli* DSM 6601. This structure was studied and published by P. E. Jansson et al., *Carbohydr. Res.* 131 (1984) 277–283. The structure corresponds to the formula shown in FIG. 2. FIG. 2 is a representation of the structure of the O antigen of *E. coli* 06. All sugars are present in the D-pyranose form. In contrast to the structure of the O-specific chain of *E. coli* 06 published by Jannson et al., the first repeating unit of the S/R mutants of *E. coli* DSM 6601 is linked by a β-glycosidic bond and was determined as such for the first time in accordance with the present invention, together with the site of substitution at the side-chain glucose ($Glc^{III}$) of the core oligosaccharide. (See FIG. 4.)

The lipid A of the coli bacteria has also been investigated by various research groups, and it was found that the structure of the lipid A generally has the hexaacyl form and is consistent for all serotypes of *E. coli* (FIG. 3). The structure of the hexaacyl compound was published in 1984 by T. Rietschel et al., Structure and Conformation of the Lipid A Component of Lipopolysaccharides. *Handbook of Endotoxins* (Proctor, R., ed.), Vol. 1, *Chemistry of Endotoxin* (E. T. Rietschel, ed.), Elsevier, Amsterdam (1984), pp. 187–220. The structure is shown in FIG. 3. FIG. 3 is a representation of the structure of the hexaacyl lipid A of *E. coli*. (Zähringer, U., Lindner, B. and E. T. Rietschel, Molecular Structure of Lipid A, the Endotoxic Center of Bacterial Lipopolysaccharides, *Adv. Carbohydr. Chem. Biochem.*, 50 (1994) 211–276). The numbers in the circles indicate the number of carbon atoms in the given fatty acid. The free hydroxyl group of the GlcN (II) represents the bonding site for the Kdo (I) of the core oligosaccharide.

The O-specific chain and the lipid A are linked by the core oligosaccharide. There are five previously known core oligosaccharides of *E. coli*; see O. Holst et al., Chemical Structure of the Core Region of Lipopolysachharide, IN: *Bacterial Endotoxic Lipopolysaccharides*, Vol. 1, Morrison, D. C. and Ryan, J. L. (eds.), Boca Raton, Fla., USA (1992) pp. 135–170 (cf. FIG. 4). FIG. 4 is a representation of the structure of the carbohydrate skeleton of the principal fraction in the core oligosaccharide of *E. coli* R1. (Vinogradov, E. V., van der Drift, K., Thomas Oates, J. E., Meshkov, S., Brade, H-. and O. Holst (1999) *Eur. J. Biochem.*, 261, 629–639.) The O-specific chain substitution at the side-chain glucose ($Glc^{III}$) and its anomerism were determined for the first time in accordance with the present invention. All sugars are present in the D-pyranose form. (L, D-Hep, L-glycero-D-manno-heptose; Kdo D-manno-oct-2-ulosonic acid; P, phosphate.)

SUMMARY OF THE INVENTION

The invention relates to lipopolysaccharides, for example, lipopolysaccharides that are extracted from *E. coli* DSM 6601. In one aspect of the present invention, a lipopolysaccharide is provided comprising a lipid A portion, a core oligosaccharide portion, and an O-specific chain having a single repeating unit of serotype 06. Preferably, the O-specific chain is linked to the core oligosaccharide portion. More preferably, the O-specific chain is linked to the core oligosaccharide by a β-glycosidic bond.

In accordance with another aspect of the invention, the linkages within the O-specific chain are linked by α-glycosidic bonds.

In another aspect of the invention, the lipid A portion of the lipopolysaccharide is linked to the core oligosaccharide portion of the lipopolysaccharide.

In another aspect of the invention, the lipopolysaccharide has eight (8) phosphate groups per molecule of lipopolysaccharide.

In another aspect of the invention, the lipopolysaccharide has a phosphate substituent P-Etn in a concentration of 0.5 moles per mole of lipopolysaccharide.

In accordance with another aspect of the invention, a process for producing lipopolysaccharides is provided. An *E. coli* bacterial mass is washed and dried, the washed and dried bacterial mass is subjected to a phenol/water extraction, and the phenol/water extract is treated with RNases, DNases and proteinase K. Preferably, the *E. coli* bacterial mass is derived from *E. coli* strain DSM 6601.

In yet another aspect of the invention, a process for the use of the lipopolysaccharide for microbiological, bioengineering, analytical, diagnostic or medical purposes is provided. Preferably, the lipopolysaccharide is *E. coli* strain DSM 6601 lipopolysaccharide.

BRIEF DESCRIPTION OF THE DRAWINGS

FIG. 1 is a photograph of the results of an SDS-PAGE analysis of *Escherichia coli* DSM 6601 LPS preparations.

FIG. 2 is a schematic drawing of the structure of the O antigen of *E. coli* 06.

FIG. 3 is a schematic drawing of the structure of the hexaacyl lipid A of *Escherichia coli*.

FIG. 5 is a representation of the results of analysis of dose-dependent IL-1 release from human monocytes induced by lipid A of *Escherichia coli* or lipid A from *E. coli* strain DSM 6601 and by LPS from S. friedenau and E. coli strain DSM 6601.

Figure 4:
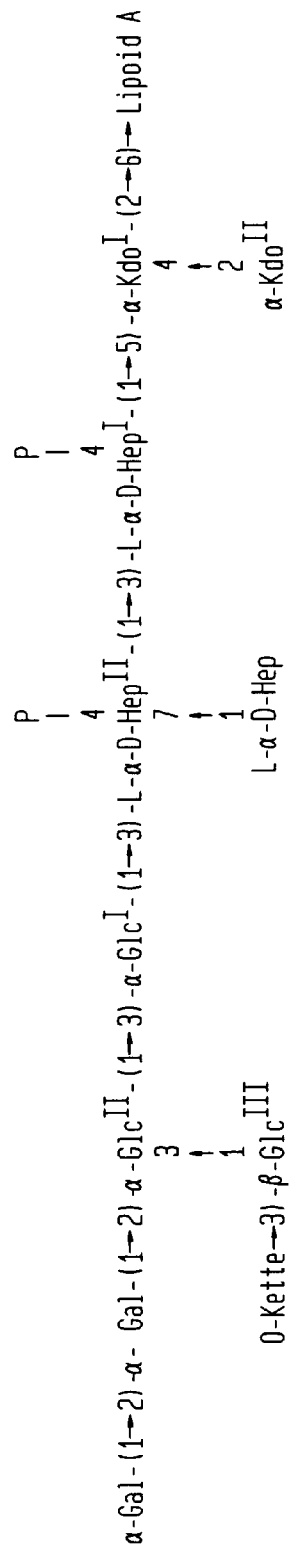
FIG. 4 is a schematic representation of the structure of the carbohydrate skeleton of the principal fraction in core oligosaccharides of *E. coli* R1.

FIG. 6 is a representation of the results of analysis of dose-dependent TNFα release from human monocytes induced by lipid A of E. coli or lipid A. from E. coli strain DSM 6601 and by LPS from S. friedenau and E. coli strain DSM 6601.

FIG. 7 is a schematic representation of the structure of a complete lipopolysaccharide of E. coli DSM 6601.

DETAILED DESCRIPTION OF PREFERRED EMBODIMENTS

Studies of the LPS of E. coli strain DSM 6601 revealed that the composition of the lipid A corresponds to the hexaacyl form of the lipid A otherwise described for E. coli.

The studies with respect to the release of IL-1 and TNFα in human monocytes confirm that this lipid A has the same activity as E. coli lipid A and therefore very probably corresponds in its structure to the known structure of E. coli lipid A (cf. FIG. 5, FIG. 6). FIG. 5 is a representation of the results of an analysis of dose-dependent IL-1 release from human monocytes induced by: 1) lipid A of Escherichia coli (top left) or lipid A from E. coli strain DSM 6601 (top right) and 2) by LPS from S. friedenau (bottom left) and Escherichia coli strain DSM 6601 (bottom right). FIG. 6 is a representation of the results of analysis of dose-dependent TNFα release from human monocytes induced by: 1) lipid A of Escherichia coli (top left) or lipid A from E. coil strain DSM 6601 (top right) and 2) by LPS from S friedenau (bottom left) and Escherichia coli strain DSM 6601 (bottom right). This assumption was confirmed by chemical analyses.

The structure of the specific O antigen of E. coli DSM 6601 is surprising due to the fact that apparently only a single repeating unit is normally present in the chain (cf. FIG. 1), which leads to the conclusion that the strain DSM 6601 is an S/R mutant, which is extremely unusual for a human isolate. However, as the serologic analysis shows, the structure of this repeating unit corresponds to the basic pattern of the O-specific chain of E. coli 06. FIG. 1 is a photograph of the results of an SDS-PAGE analysis of E. coli DSM 6601 (16% separation gel). Lane 1 is an LPS preparation 1 (phenol/water extract UM II.82); lane 2 is LPS preparation 2; lane 3 is LPS preparation 3; lane 4 is free; lane 5 is E. coli 0111 LPS; lane 6 is Pseudomonas aeruginosa Fischer type 2 LPS; lane 7 is Salmonella minnesota R60 LPS. Arrows point to the LPS bands of core oligosaccharide and a repeating unit (R/S mutant, arrow A) and to an LPS with a complete core oligosaccharide (arrow B).

Although the core region in strain DSM 6601 corresponds to the well-known R1 structure, structural peculiarities are present. Specifically, 8 phosphate groups were analytically determined per LPS molecule, and the lipid A generally has only 2 phosphate groups. Furthermore, a nonstoichiometric content of pyrophosphoethanolamine was found.

Therefore, the LPS of the strain DSM 6601 differs significantly from the previously known LPS from E. coli, especially with respect to the phosphorylated sugar moiety of the core and the degree of polymerization of the O-specific chain. The lipid A corresponds structurally and biologically to the usual type for E. coli. The LPS described here not only is well suited for identifying the coli strain that carries it, but also reduces the pathogenicity of the coli strain while allowing it to retain its immunomodulatory effect. The fact that the O-specific chain is linked by a β-glycosidic bond instead of an α-glycosidic bond could be clearly shown for the first time for E. coli with the example of the S/R mutant DSM 6601.

The lipopolysaccharide (LPS) of E. coli DSM 6601 is a new smooth-rough (S/R) structure, which, on the one hand, is composed of previously known partial structures (O-specific chain, core oligosaccharide and lipid A) and, on the other hand, was completely structurally characterized for the first time in the complex form that exists here (cf. FIG. 7). The O-specific chain, which consists of only a single repeating unit of the serotype 06, is linked to the core oligosaccharide by a β-glycosidic bond, which differs from the linkages within the O-specific chain (α-glycosidic). The core oligosaccharide has the R1 structure, a chemical finding that is confirmed by serologic tests with R1-specific antibodies. The lipid A component has a specific chemical structure that is characteristic of E. coli lipid A.

The LPS of E. coli strain DSM 6601 exhibits astonishing homogeneity. Heterogeneity can be observed only with respect to the phosphate substituents (PP and P-Etn vs. P and P), which is being described in this form for the first time. The P-Etn substituent could be definitely determined in the core oligosaccharide, the R1-core oligosaccharide, at the 2 position of the second heptose ($Hep^{II}$) by complex NMR analyses.

The complete structure of the LPS of the strain DSM 6601 is shown in FIG. 7. FIG. 7 is a representation of the structure of the complete lipopolysaccharide of E. coli DSM 6601. The phosphate substituents P and Etn in the two heptoses $Hep^{I}$ and $Hep^{II}$ are not stoichiometric in the core oligosaccharide and are therefore indicated by a broken line. The position and anomeric bond of the $Kdo^{I}$ to the lipid A are analogous to other E. coli LPS structures, likewise the position and anormeric bond of the $Kdo^{II}$.

The invention is explained in greater detail below by examples.

EXAMPLE 1

Preparation of the LPS

The LPS was obtained from the washed and dried bacterial mass by a modified phenol/water extraction; for further details on this aspect of the preparation, see O. Westphal et al., Bacterial Lipopolysaccharides, Extraction with Phenol-Water and Further Applications of the Procedure, Meth. Carbohydr. Chem., Vol. V (1965), pp. 83–91.

47 g of the lyophilized bacteria, which had first been washed twice with distilled water, were extracted by a modified method of Westphal and Jann. The modification consisted in a subsequent enzyme treatment (DNase, RNase, proteinase K) of the aqueous extract, the purpose of which was to remove possible foreign proteins and DNA/RNA components. To this end, the aqueous phase (about 1.2 L) is treated at room temperature with 20 mg of RNase (ribonuclease A, bovine pancreas, Sigma) and 20 mg of DNase (DNase I, bovine pancreas, grade II, Sigma). The mixture is stirred for 30 h at room temperature, treated with 20 mg of proteinase K (Tritirachium album, Boehringer, Mannheim), and stirred for another 12 h. The suspension is dialyzed three times against 15 L of distilled water over 24 h at 4° C. and then lyophilized. The enzyme-treated extract is resuspended in distilled water to an end concentration of 50 mg/mL. This suspension is ultracentrifuged three times at low temperature (155,000×g, 4° C., 4 h). The sediment (LPS) is suspended in 150 mL of distilled water, dialyzed again for three days against water, and then lyophilized (yield of LPS: 1.45 g, 3.1% m/m).

EXAMPLE 2

Analysis of the LPS Extracted From *E. coli* Strain DSM 6601

Hexosamine (HexN) (meaning here glucosamine+ galactosamine, GlcN+GalN) was determined by the modified Morgan-Elson test (Strominger, J. L., Park, J. T., Thompson, R. E., *J. Biol. Chem.* 234, 3263–3268 (1959)) or alternatively by HPLC (PICO-TAG, Waters). In contrast to the Morgan-Elson test, in this analytical method, it is possible not only separately to determine and quantify GlcN and GalN, but also to make parallel determinations of the presence of GlcN phosphate, 2-ethanolamine (Etn) and 2-ethanolamine phosphate (Etn-P), which often occur in LPS. Gas-liquid chromatography (GC) was performed in a Varian 3700 GC or Hewlett Packard (HP 5890 Series II) gas chromatograph on a capillary column (fused-silica SPB-5®, 30 m, Supelco). The combined gas-liquid chromatography/mass spectrometry (GC-MS) was performed in a mass spectrometer (HP model 5989) equipped with an HP-1 capillary column (30 m, Hewlett Packard). The GC and GC-MS analyses were used to determine the neutral sugars (Glc, Gal, Hep, Man) as their alditol acetates (Sawardeker, J. S., Slonerker, J. H., Jeanes, A., *Anal. Chem.* 37, 1602–1604 (1967)) and to determine and quantify the fatty acids as their fatty acid methyl ester derivatives after intense methanolysis (2 M HCl/MeOH, 120° C., 16 h) (Wollenweber, H.-W. and Rietschel, E. T., Analysis of Lipopolysaccharide (Lipid A) Fatty Acids, *J. Microbiol. Meth.* 11, (1990) 195–211) and extraction with chloroform. In both GC analytical methods, the initial temperature was 150° C. (isothermal for 3 min), and then the temperature was increased to 320° C. by a linear temperature gradient of 5° C./min. Phosphate was determined by the method of Lowry et al. (Lowry, O. H., Roberts, N. R. , Leiner, K. Y., Wu, M. Kl., Farr, A. L., *J. Biol. Chem.* 207, 1–17 (1954)), and the 2-keto-3-deoxy-D-manno-octulosonic acid (Kdo) was determined by the thiobarbituric acid test (Waravdekar, V. C. and Saslaw, L. D., *J. Biol. Chem.* 234, 1945–1950 (1959)).

Preparation and Purification of the Free Lipid A and the Core Oligosarcharide LPS (258.8 mg) was suspended in 25 mL of 0.1 M NaOAc/HOAc (ph 4.4) and subjected to gentle acid hydrolysis at 100° C. for 1 h. The lipophilic fraction (lipid A) was then extracted three times from the hydrolysate with 25 mL of chloroform (yield: 23.2 mg). The lipid A from the organic phase was further purified by preparative thin-layer chromatography (PTLC) (2 mm PTLC silica gel 60 plate, E. Merck, Darmstadt), which was chromatographed with chloroform-methanol-water 100:75:15 (v/v/v) and developed by immersion in distilled water. In this way, six fractions were obtained, of which the principal fraction ($R_f \sim 0.4$) represents the purified diphosphorylated hexaacyl lipid A (DPHLA-Ec$_{6601}$). The purified DPHLA-EC$_{6601}$ (yield: 2.06 mg) was dissolved in chloroform-methanol 8:2 (v/v) and treated with ion exchanger (Amberlite IRA 120, H$^+$ form) before the MALDI-TOF-MS. An aliquot portion (250 $\mu$g) of the purified DPHLA-EC$_{6601}$ was used for the biological experiments.

The aqueous phase from the chloroform extraction was lyophilized (yield: 272 mg), and the oligosaccharide was further purified by means of a TSK column [3.5×90 cm, TSK HW-40(S), E. Merck] in pyridine-acetic acid-water 8:20:2000 (v/v/v). The individual oligosaccharide fractions (pool A, B, C, D) were analyzed by GC-MS and NMR spectroscopy. The principal fraction (pool A, #28–41; 49.05 mg), which contained both sugar components of the O-specific chain (Man, GalNac) and sugar components of the core oligosaccharide (Hep, Kdo), was further purified. The other fractions contained monosaccharides, artifacts of Kdo (anhydro- and lactones), which were not further analyzed, and, finally, salt. The principal fraction of the TSK separation showed all components of the core oligosaccharide (Kdo, Gal, Hep) and of the O-specific chain (Man, GalNac) in both the GC-MS analysis and the NMR analysis and therefore was worked up further.

Whether analytical high-pressure anion-exchange chromatography (HPAEC) is suitable for purifying the oligosaccharides to homogeneity was determined. A specific HPLC method for the analysis of complex sugar structures (DIONEX system) with an analytical CarboPac PAl column (4.6 mm×250 mm) and a linear salt gradient (5 min at 0 M NaOAc, then increased to 0.5 M NaOAc in 50 min) at a flow rate of 1 mL/min was used. The eluate was detected by a pulse-amperometric detector (PAD) for reduction equivalences (sugar molecules). Four oligosaccharide fractions were obtained in this way, which were then similarly further purified by semipreparative HPAEC.

The semipreparative HPAEC was carried out with a CarboPac PA1 column [(9 mm×250 mm) Dionex system] with the same salt gradient as in the analytical HPAEC (5 min at 0 M NaOAc, then increased to 0.5 M NaOAc in 50 min) and a flow rate of 4 mL/min. The application of the oligosaccharide (42 mg; pool A from the TSK column) to the semipreparative HPAEC column was performed in two analogous HPAEC runs. The eluate was collected in fractions of one minute each, and the individual fractions were analyzed by analytical HPAEC. Two principal fractions were obtained in this way by semipreparative HPAEC (fraction I, retention time $t_R \sim 12$ min and fraction II, $t_R \sim 15$ min). The salt had to be removed from both HPAEC fractions by means of a G-10 column (2.5×120 cm) before the MALDI-TOF-MS and NMR analysis (yield: fraction I: 4.68 mg; fraction II: 4.39 mg).

Matrix-assissted Laser Desorption/Ionization Time-of-flight (MALDI-TOF) Mass Spectrometry Matrix-assisted laser desorption/ionization time-of-flight mass spectrometry (MALDI-TOF-MS) was recorded in a Bruker-Reflex$^{II}$ time-of-flight spectrometer (Bruker-Franzen Analytik, Bremen) exclusively in the linear configuration and in the negative mode at an accelerating voltage of 20 kV and with delayed ion extraction. The samples were first dissolved in chloroform (lipid A) or distilled water (oligosaccharide fractions) in a concentration of 10 $\mu$g/$\mu$L. 2-$\mu$L aliquots of these solutions were dissolved with 2 $\mu$L of a matrix solution consisting of 0.5 M 2,4,6-trihydroxyacetophenone (Aldrich, Steinheim) in methanol. Aliquots (0.5 $\mu$L) of this mixture were applied to a metal holder and dried with a hair drier.

NMR Spectroscopy

One-dimensional (1D) $^1$H- and $^{31}$P-NMR spectra and two-dimensional (2D) NMR spectra were recorded with a Bruker Avance DRX-600 spectrometer (Bruker, Rheinstetten), and $^{13}$C NMR spectra were recorded with a Bruker AMX-360 spectrometer at 300 K in $^2$H$_2$O. Before each measurement, the samples were lyophilized twice with heavy water ($^2$H$_2$O). Acetone ($\delta_H$ 2.225 ppm, $\delta_C$ 31.45 ppm) or 85% H$_3$PO$_4$ ($\delta_P$ 0 ppm) was used as the external reference signal. Standard Bruker software (XWINNMR 1.3) was used to record the NMR data. The mixing times for the TOCSY (total correlated spectroscopy) and NOESY (nuclear Overhauser enhancement spectroscopy) were 100 and 500 ms, respectively.

Serologic Analyses

The serologic analyses were performed as Western blots, which were developed with three different antibodies.

Polyclonal anti-06 antiserum (rabbit) was prepared with E. coli strain DSM 6601 (serotype 06: K5: H1) at the Institute of Hygiene in Hamburg (Prof. Bockemühl).

Polyclonal anti-E. coli R1-antiserum (rabbit, internal designation: K299/d58) was obtained by immunization with a rough-form mutant that possesses an R1-core (anti-R1).

A monoclonal antibody (WN1-222-5, internal designation: F 167) was used, which broadly cross-reacts against all E. coli core oligosaccharides above a minimal structure (>Rd).

TABLE

Component analysis of E. coli LPS extracted from the strain DSM 6601.

| Component Carbohydrates | Amount of the component nmoles/mg (moles/LPS)[a] Analysis 1 | Analysis 2 |
|---|---|---|
| GlcN[b] | 283 (1.8) | not determined |
| GalN | 139 (0.9) | not determined |
| HexN[c] | 591 (3.8) | 589 (2.9) |
| Kdo | 248 (1.6) | 242 (1.2) |
| Man | 321 (2.1) | 383 (1.9) |
| Gal | 474 (3.0) | 557 (2.8) |
| Glc | 1069 (6.9) | 1291 (6.4) |
| L,D-Hep | 566 (3.6) | 442 (2.2) |
| Polar Head Groups | | |
| P | 1188 (7.6) | 1146 (5.7) |
| Etn-P | 85 (0.5) | not determined |
| Fatty Acids | | |
| 12:0 | 130 (0.8) | 162 (0.8) |
| 14:0 | 156 (1.0) | 201 (1.0) |
| 14:0(3-OH) | 460 (3.0) | 504 (2.5) |
| 16:0 | Traces | traces |

[a]The molar ratio of the individual components in parentheses) was standardized to the value of myristic acid (14:0) (1.0 mole 14:0/mole LPS)due to the presence of GalNac and GlcNac in the O-specific chain.
[b]GlcN determined by amino acid analyzer. The value is obtained from the sum of GlcN and GlcN-6P.
[c]HexN photometrically determined by the Morgan-Elson test.

The LPS preparations obtained by the method described above and comparative samples of LPS were subjected to polyacrylamide gel electrophoresis (cf. FIG. 1). In the preparation of the SDS-PAGE analysis of the LPS, we worked with 16% polyacrylamide gels (U.K., Laemmli, Cleavage of Structural Proteins during Assembly of Head of Bacteriophage T4, Nature, 227, 680–685 (1970)). The LPS bands were stained by the sensitive alkaline silver stain method (C. M. Tsai and Frasch, C. F., A Sensitive Silver Stain for Detecting Lipopolysaccharides in Polyacrylamide Gels, Anal. Biochem., 119, 1982, 115–119).

The results of the analyses are shown in FIG. 1.

EXAMPLE 3

Biological Activity (a) IL-1 Activity

The IL-1 activity is determined by an MNC proliferation assay in a culture supernatant. Human monocytes (MNC) are isolated from the peripheral blood of volunteer donors ($8 \times 10^5$ MNC/200 mL), transferred into a glass and simultaneously treated with test substance. To test the biological activity in vitro, the cells are first stimulated with LPS (10 ng/mL). After an incubation period of 8 hours, 150 mL of the culture supernatant are analyzed for cytokine release. The IL-1 activity is determined by a fibroblast proliferation assay in a culture supernatant. The fibroblasts needed for this were obtained from human prepuce. The proliferation of these fibroblasts was increased by IL-1. The biological activity in the culture supernatant is determined by comparing the dose-response curve of the culture supernatant with the curve of the standard in a probit analysis. The LPS from a bacterial strain known to be endotoxically active (Salmonella friedenau) serves as the reference (positive control) and therefore is included in FIG. 5.

(b) TNFα Activity

The TNFα activity in a culture supernatant is determined in a cytotoxicity assay with the TNF-sensitive cell line L929. The TNF activity can be determined by comparing the dos-response curve of the culture supernatant with the curve of the standard in a probit analysis. Here again, a Salmonella friedenau LPS that is known to be endotoxically active serves as the positive control. The results are graphically represented in FIG. 6.

The results show that, with respect to IL-1 and TNFα release, there are no significant differences between the LPS from Salmonella friedenau, which serves as the standard and positive control, and the LPS from the strain DSM 6601 (FIGS. 5 and 6, lower graphs) This is also confirmed by the fact that the lipid A of the strain DSM 6601 shows virtually the same activity as the highly purified lipid A of E. coli (FIGS. 5 and 6, upper graphs).

All embodiments of the invention have been described by way of illustration, and will be understood that the invention can be carried out by persons skilled in the art with many modifications, variations and adaptations, without departing from its spirit or exceeding the scope of the claims.

What is claimed is:

1. A lipopolysaccharide comprising:
   a) a lipid A portion; and
   b) a core oligosaccharide portion; and
   c) an O-specific chain having a single repeating unit of serotype O6.

2. The lipopolysaccharide of claim 1, wherein the O-specific chain is linked to said core oligosaccharide portion.

3. The lipopolysaccharide of claim 1, wherein the O-specific chain is linked to the core oligosaccharide by a β-glycosidic bond.

4. The lipopolysaccharide of claim 1, wherein linkages within the O-specific chain are linked by α-glycosidic bonds.

5. The lipopolysaccharide of claim 1, wherein the lipid A portion is linked to the core oligosaccharide portion.

6. The lipopolysaccharide of claim 1, having eight (8) phosphate groups per molecule of lipopolysaccharide.

7. The lipopolysaccharide of claim 1, having a phosphate substituent P-Etn in a concentration of 0.5 moles per mole of lipopolysaccharide.

8. A process for producing the lipopolysaccharide of claim 1, comprising:
   a) washing and drying an E. coli bacterial mass;
   b) subjecting the mass to a phenol/water extraction;
   c) treating the phenol/water extract with RNases, DNases and proteinase K.

9. The process of claim 8, wherein the E. coli is E. coli strain DSM 6601.

* * * * *